(12) United States Patent
Pacheco et al.

(10) Patent No.: US 9,700,698 B2
(45) Date of Patent: Jul. 11, 2017

(54) COMPONENTS AND METHODS FOR A CATHETER POSITIONING SYSTEM WITH A SPREADER AND TRACK

(71) Applicant: Catheter Precision, Inc., Ledgewood, NJ (US)

(72) Inventors: Robert Pacheco, Bayside, NY (US); Steve Foley, Kerrville, TX (US); David Jenkins, Budd Lake, NJ (US)

(73) Assignee: CATHETER PRECISION, INC., Ledgewood, NJ (US)

( * ) Notice: Subject to any disclaimer, the term of this patent is extended or adjusted under 35 U.S.C. 154(b) by 199 days.

(21) Appl. No.: 14/494,693

(22) Filed: Sep. 24, 2014

(65) Prior Publication Data
US 2015/0094653 A1 Apr. 2, 2015

Related U.S. Application Data

(60) Provisional application No. 61/883,298, filed on Sep. 27, 2013.

(51) Int. Cl.
*A61M 25/01* (2006.01)
*A61B 17/00* (2006.01)
*A61B 34/30* (2016.01)

(52) U.S. Cl.
CPC ......... *A61M 25/0113* (2013.01); *A61B 34/30* (2016.02); *A61B 2017/00212* (2013.01);
(Continued)

(58) Field of Classification Search
CPC .... A61B 2017/00212; A61B 2034/301; A61B 34/30; A61M 2025/0166; A61M 25/0111; A61M 25/0113
See application file for complete search history.

(56) References Cited

U.S. PATENT DOCUMENTS

| 4,549,538 A | 10/1985 | Schadrack, III et al. |
| 4,721,123 A | 1/1988 | Cosentino et al. |

(Continued)

FOREIGN PATENT DOCUMENTS

| JP | 2007527296 A | 9/2007 |
| WO | 2005087128 A1 | 9/2005 |

(Continued)

OTHER PUBLICATIONS

WIPO, International Preliminary Report on Patentability; PCT/US2006/027024; Jan. 16, 2008; 8pgs.
(Continued)

*Primary Examiner* — Quynh-Nhu H Vu
(74) *Attorney, Agent, or Firm* — The Marbury Law Group, PLLC

(57) ABSTRACT

Embodiments include a spreader and a resealable delivery channel in a catheter positioning system configured to introduce a catheter into the resealable delivery channel. The spreader may have shapes configured to help users insert the spreader and a catheter into the resealable delivery channel and to retain the spreader and the catheter within the resealable delivery channel. The resealable delivery channel may be shaped to accommodate the spreader or catheter. The resealable delivery channel may include flexible plastic lips that are moveable to facilitate insertion of the spreader and a catheter into the resealable delivery channel.

12 Claims, 15 Drawing Sheets

(52) U.S. Cl.
CPC .... *A61B 2034/301* (2016.02); *A61M 25/0111* (2013.01); *A61M 2025/0166* (2013.01)

(56) References Cited

U.S. PATENT DOCUMENTS

| | | | |
|---|---|---|---|
| 5,226,892 A | 7/1993 | Boswell | |
| 5,644,551 A | 7/1997 | Carmichael et al. | |
| 5,649,956 A | 7/1997 | Jensen et al. | |
| 5,682,890 A | 11/1997 | Kormos et al. | |
| 5,810,880 A | 9/1998 | Jensen et al. | |
| 5,814,038 A | 9/1998 | Jensen et al. | |
| 5,855,583 A | 1/1999 | Wang et al. | |
| 6,007,550 A | 12/1999 | Wang et al. | |
| 6,063,095 A | 5/2000 | Wang et al. | |
| 6,080,181 A | 6/2000 | Jensen et al. | |
| 6,096,004 A | 8/2000 | Meglan et al. | |
| 6,132,368 A | 10/2000 | Cooper | |
| 6,171,234 B1 | 1/2001 | White et al. | |
| 6,171,277 B1 | 1/2001 | Ponzi | |
| 6,200,315 B1 | 3/2001 | Gaiser et al. | |
| 6,346,072 B1 | 2/2002 | Cooper | |
| 6,396,232 B2 | 5/2002 | Haanpaa et al. | |
| 6,398,755 B1 | 6/2002 | Belef et al. | |
| 6,413,264 B1 | 7/2002 | Jensen et al. | |
| 6,445,984 B1 | 9/2002 | Kellogg | |
| 6,461,372 B1 | 10/2002 | Jensen et al. | |
| 6,527,782 B2 | 3/2003 | Hogg et al. | |
| 6,620,174 B2 | 9/2003 | Jensen et al. | |
| 6,726,675 B1 | 4/2004 | Beyar | |
| 6,788,999 B2 | 9/2004 | Green | |
| 6,850,817 B1 | 2/2005 | Green | |
| 6,963,792 B1 | 11/2005 | Green | |
| 6,974,465 B2 | 12/2005 | Belef et al. | |
| 6,999,852 B2 | 2/2006 | Green | |
| 7,006,895 B2 | 2/2006 | Green | |
| 7,090,683 B2 | 8/2006 | Brock et al. | |
| 7,118,582 B1 | 10/2006 | Wang et al. | |
| 7,169,141 B2 | 1/2007 | Brock et al. | |
| 7,204,844 B2 | 4/2007 | Jensen et al. | |
| 7,214,230 B2 | 5/2007 | Brock et al. | |
| 7,276,044 B2 | 10/2007 | Ferry et al. | |
| 7,314,230 B2 | 1/2008 | Kumagai et al. | |
| 7,331,967 B2 | 2/2008 | Lee et al. | |
| 7,357,774 B2 | 4/2008 | Cooper | |
| 7,371,210 B2 | 5/2008 | Brock et al. | |
| 7,377,906 B2 | 5/2008 | Selkee | |
| 7,537,570 B2 | 5/2009 | Kastelein | |
| 7,630,752 B2 | 12/2009 | Viswanathan | |
| 7,648,513 B2 | 1/2010 | Green et al. | |
| 7,758,564 B2 | 7/2010 | Long et al. | |
| 8,046,049 B2 | 10/2011 | Govari et al. | |
| 8,672,880 B2 | 3/2014 | Cohen et al. | |
| 2001/0053879 A1 | 12/2001 | Mills et al. | |
| 2002/0042620 A1 | 4/2002 | Julian et al. | |
| 2002/0072704 A1 | 6/2002 | Mansouri-Ruiz | |
| 2002/0120254 A1 | 8/2002 | Julian et al. | |
| 2002/0177789 A1 | 11/2002 | Ferry et al. | |
| 2002/0183723 A1* | 12/2002 | Belef | A61B 8/12 606/1 |
| 2004/0077942 A1 | 4/2004 | Hall et al. | |
| 2004/0254566 A1 | 12/2004 | Plicchi et al. | |
| 2005/0038412 A1 | 2/2005 | Rabiner et al. | |
| 2005/0065435 A1 | 3/2005 | Rauch et al. | |
| 2005/0113719 A1 | 5/2005 | Saadat | |
| 2005/0203382 A1 | 9/2005 | Govari et al. | |
| 2005/0209614 A1 | 9/2005 | Fenter et al. | |
| 2005/0222554 A1 | 10/2005 | Wallace et al. | |
| 2005/0228440 A1 | 10/2005 | Brock et al. | |
| 2005/0277874 A1 | 12/2005 | Selkee | |
| 2005/0283140 A1 | 12/2005 | Jensen et al. | |
| 2006/0009735 A1 | 1/2006 | Viswanathan et al. | |
| 2006/0041181 A1 | 2/2006 | Viswanathan et al. | |
| 2006/0084911 A1 | 4/2006 | Belef et al. | |
| 2006/0084945 A1 | 4/2006 | Moll et al. | |
| 2006/0095022 A1 | 5/2006 | Moll et al. | |
| 2006/0161136 A1 | 7/2006 | Anderson et al. | |
| 2006/0161137 A1 | 7/2006 | Orban et al. | |
| 2006/0161138 A1 | 7/2006 | Orban et al. | |
| 2006/0167441 A1 | 7/2006 | Wang et al. | |
| 2006/0178559 A1 | 8/2006 | Kumar et al. | |
| 2006/0229587 A1 | 10/2006 | Beyar | |
| 2006/0235436 A1 | 10/2006 | Anderson et al. | |
| 2006/0270915 A1 | 11/2006 | Ritter et al. | |
| 2006/0293643 A1 | 12/2006 | Wallace et al. | |
| 2007/0012135 A1 | 1/2007 | Tierney et al. | |
| 2007/0016174 A1 | 1/2007 | Millman et al. | |
| 2007/0019330 A1 | 1/2007 | Wolfersberger | |
| 2007/0021776 A1 | 1/2007 | Jensen et al. | |
| 2007/0043338 A1 | 2/2007 | Moll et al. | |
| 2007/0043455 A1 | 2/2007 | Viswanathan et al. | |
| 2007/0149946 A1 | 6/2007 | Viswanathan et al. | |
| 2007/0233044 A1 | 10/2007 | Wallace et al. | |
| 2007/0239172 A1 | 10/2007 | Lee et al. | |
| 2007/0250073 A1 | 10/2007 | Brock et al. | |
| 2007/0250074 A1 | 10/2007 | Brock et al. | |
| 2007/0260115 A1 | 11/2007 | Brock et al. | |
| 2007/0276423 A1 | 11/2007 | Green | |
| 2007/0283263 A1 | 12/2007 | Zawde et al. | |
| 2007/0299479 A1 | 12/2007 | Saksena | |
| 2008/0009791 A1 | 1/2008 | Cohen et al. | |
| 2008/0039869 A1 | 2/2008 | Mills et al. | |
| 2008/0045892 A1 | 2/2008 | Ferry et al. | |
| 2008/0059598 A1 | 3/2008 | Garibaldi et al. | |
| 2008/0119824 A1 | 5/2008 | Weitzner et al. | |
| 2008/0119872 A1 | 5/2008 | Brock et al. | |
| 2008/0125793 A1 | 5/2008 | Brock et al. | |
| 2008/0125794 A1 | 5/2008 | Brock et al. | |
| 2008/0140087 A1 | 6/2008 | Barbagli | |
| 2008/0147091 A1 | 6/2008 | Cooper | |
| 2008/0183136 A1 | 7/2008 | Lenker et al. | |
| 2008/0215065 A1 | 9/2008 | Wang et al. | |
| 2008/0245946 A1 | 10/2008 | Yu | |
| 2008/0249536 A1 | 10/2008 | Stahler et al. | |
| 2008/0300592 A1 | 12/2008 | Weitzner et al. | |
| 2009/0012533 A1 | 1/2009 | Barbagli et al. | |
| 2009/0082722 A1 | 3/2009 | Munger et al. | |
| 2009/0105639 A1 | 4/2009 | Weitzner et al. | |
| 2009/0105645 A1 | 4/2009 | Kidd et al. | |
| 2009/0248043 A1 | 10/2009 | Tierney et al. | |
| 2010/0010475 A1 | 1/2010 | Teirstein et al. | |
| 2010/0256558 A1 | 10/2010 | Olson et al. | |
| 2011/0077590 A1 | 3/2011 | Plicchi et al. | |
| 2011/0105954 A1* | 5/2011 | Cohen | A61M 25/0133 600/585 |
| 2012/0182134 A1 | 7/2012 | Doyle | |
| 2012/0184955 A1* | 7/2012 | Pivotto | A61B 19/2203 606/41 |
| 2012/0197182 A1 | 8/2012 | Millman et al. | |
| 2012/0220931 A1 | 8/2012 | Cohen et al. | |
| 2013/0138118 A1 | 5/2013 | Doyle | |

FOREIGN PATENT DOCUMENTS

| | | |
|---|---|---|
| WO | 2007008967 A2 | 1/2007 |
| WO | 2009092059 A2 | 7/2009 |

OTHER PUBLICATIONS

State Intellectual Property Office of the People's Republic of China, First Office Action, Oct. 30, 2009, Chinese Patent Application 200680025512.7, "Remotely Controlled Catheter Insertion System," with English translation, (24 pgs. total).

Chinese Application 200680025512.7, State Intellectual Property Office of the People's Republic of China, Office Action dated Feb. 13, 2012.

Chinese Application 200980102420.8, State Intellectual Property Office of the People's Republic of China, Office Action dated Feb. 16, 2012.

International Preliminary Report on Patentability, Intl Application PCT/US2009/031357. International Bureau of WIPO, Jul. 29, 2010.

(56) References Cited

OTHER PUBLICATIONS

International Search Report and Written Opinion, Intl Application PCT/US2009/031357. International Search Authority, U.S. Patent and Trademark Office (ISA/US), Mar. 19, 2009.
U.S. Appl. No. 13/051,736, Final Office Action dated Nov. 5, 2012.
Hein et al., "Robot Supported Insertion of Catheters for Hyperthermia and Branch Therapy," Computer Assisted Radiology and Surgery, 1998, pp. 660-663.
Macoviak, "Catheter System for Surgical Access and Circulatory Support of the Heart," USPTO, Official Gazette, vol. 1278, Jan. 6, 2004.
U.S. Appl. No. 13/051,736, Non-Final Office Action dated Jul. 17, 2012.
U.S. Appl. No. 12/903,397, Non-Final Office Action dated Nov. 19, 2012.
Canadian Application 2,646,846, Office Action dated Sep. 19, 2012.
Extended European Search Report of Apr. 17, 2013; European Application No. 09702983.9.
Japanese Patent Application No. 2010-543298; Office Action of Mar. 19, 2013.
U.S. Appl. No. 13/461,463, Final Office Action dated Jun. 27, 2014.
U.S. Appl. No. 13/461,463, Non-Final Office Action dated Oct. 31, 2014.
U.S. Appl. No. 12/515,005, Non-Final Office Action dated Apr. 11, 2013.
U.S. Appl. No. 13/078,663, Non-Final Office Action dated Aug. 14, 2014.

\* cited by examiner

COMPONENTS AND METHODS FOR A CATHETER POSITIONING SYSTEM WITH A SPREADER AND TRACK

CROSS-REFERENCE TO RELATED APPLICATIONS

The present application claims the benefit of priority to U.S. Provisional Patent Application No. 61/883,298, entitled "COMPONENTS AND METHODS FOR A CATHETER POSITIONING SYSTEM WITH A SPREADER AND TRACK," filed Sep. 27, 2013, the entire contents of which are incorporated herein by reference.

BACKGROUND

Many invasive medical procedures require the use of radiation to visualize and track the location of an inserted device. For example, procedures involving catheter insertion, such as invasive electrophysiology procedures, rely on fluoroscopy or other radioactive imaging techniques to help navigate and position the catheter within a patient's body at a particular site, such as in the heart or inside a blood vessel in the circulatory system.

High dosages of radiation may have long term adverse health effects. A patient may be directly exposed only once or twice to radiation during such procedures and avoid such adverse effects. However, physicians, medical technicians and staff can experience a large cumulative radiation dosage over time, both directly and indirectly, from conducting many procedures.

To protect the operator and staff from this radiation, shielding such as lead aprons, gowns, glasses, skirts, etc., is worn. Such lead clothing, especially a lead apron, is quite heavy and uncomfortable, and its use has been associated with cervical and lumbar spine injury or degradation.

SUMMARY OF THE INVENTION

Various embodiments include a catheter positioning system having a resealable delivery channel configured to guide a catheter as the catheter positioning system advances or retracts the catheter with respect to a patient. The catheter may be inserted into the resealable delivery channel, such as through a resealing groove with flexible plastic lips running along the top of the delivery channel. A spreader may spread the flexible plastic lips and guide the catheter into the resealable delivery channel. In various embodiments, part or all of the spreader may move with the catheter during positioning, such as rotating with the catheter. The various embodiments include spreaders of various shapes configured to help users insert the catheter into and remove the catheter from the flexible plastic lips of the resealable delivery channel. In one embodiment the spreader includes flange shaped tip, and in another embodiment, the spreader includes a bulb shaped tip.

In further embodiments, the resealable delivery channel may be shaped to accommodate the spreader or catheter. For example, the flexible plastic lips may be deflected in certain directions. In alternate embodiments, the flexible plastic lips may be adjustable such that a user can move them in various directions.

BRIEF DESCRIPTION OF THE DRAWINGS

The accompanying drawings, which are incorporated herein and constitute part of this specification, illustrate exemplary embodiments of the invention, and together with the general description given above and the detailed description given below, serve to explain the features of the invention.

DETAILED DESCRIPTION

Figure 1:
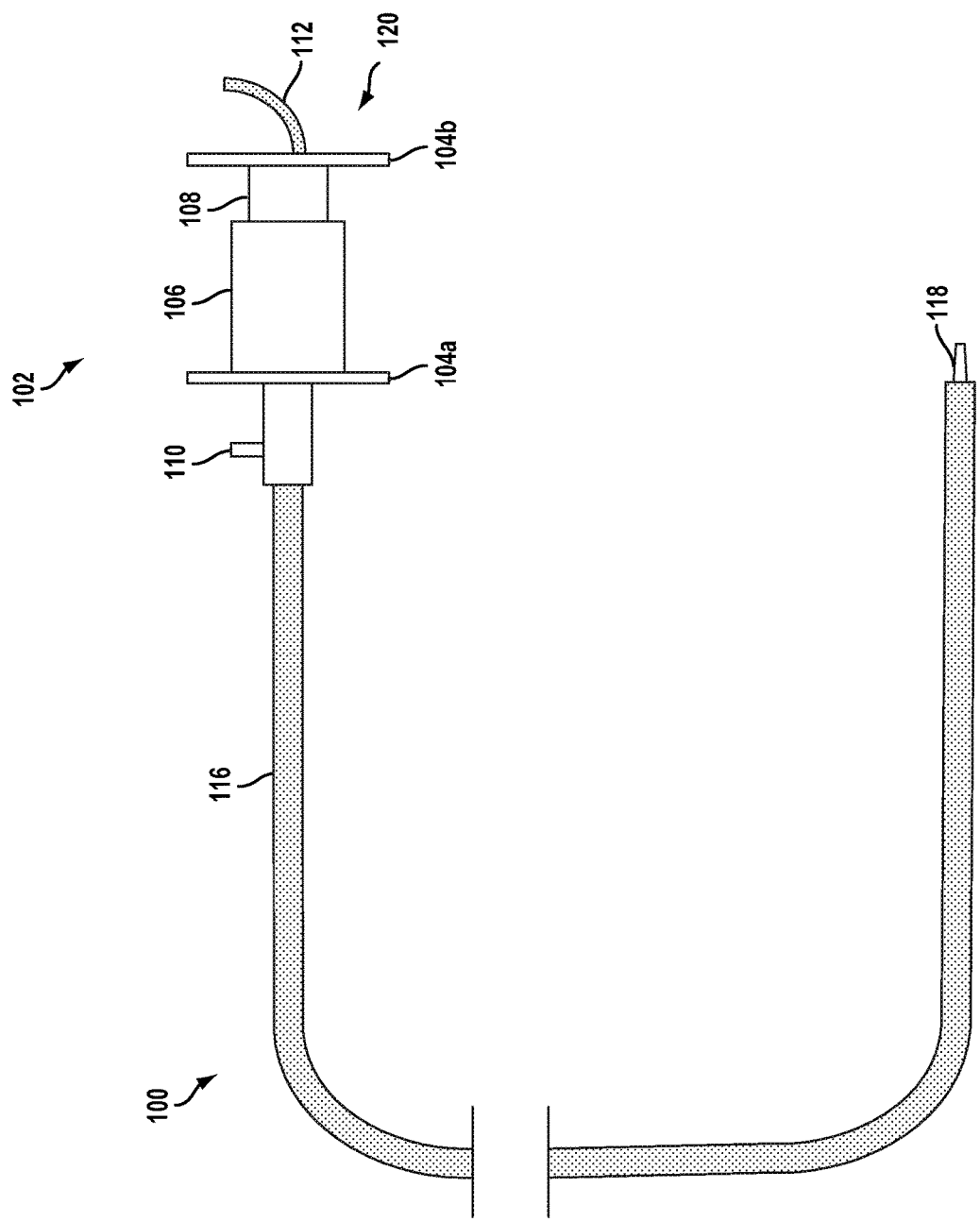
FIG. 1 is a top view of a catheter suitable for use in the various embodiments.

Various embodiments will be described in detail with reference to the accompanying drawings. Wherever possible, the same reference numbers will be used throughout the drawings to refer to the same or like parts. References made to particular examples and implementations are for illustrative purposes and are not intended to limit the scope of the invention or the claims.

Various embodiments provide improved components for introducing a catheter into a resealable delivery channel within a catheter positioning system. The catheter positioning system enable a physician to remotely control manipulation and insertion of a catheter into a patient while being positioned away from sources of radiation used for imaging or other procedures. The catheter positioning system may be used to move an attached catheter, such as advancing or retracting the catheter in relation to a patient or within a patient's body in response to control inputs on a remote controller. The catheter positioning device may also be used to actuate the catheter, such as by controlling an actuator on a catheter's handle. Catheter actuators may perform various tasks, such as deflecting a tip to help in navigation or controlling one or more transducers to assist in an operation.

In various embodiments, the catheter positioning system includes a resealable delivery channel configured to guide the catheter as the catheter positioning system advances or retracts the catheter. The resealable delivery channel helps to prevent the catheter from buckling as it is advanced into the patient. The resealable delivery channel may further help to maintain a sterility boundary between the operating mechanisms of the catheter positioning system and the operative parts of the catheter, which may come into contact with the patient. The catheter may be inserted into the resealable delivery channel through a resealing groove with flexible plastic lips running along the top of the delivery channel. A spreader is used to spread the flexible plastic lips and guide the catheter into the resealable delivery channel. The flexible plastic lips may include one or more entry holes to enable the spreader to slide into the resealable delivery channel. Part or all of the spreader may move with the catheter during positioning, such as rotating with the catheter. The resealable delivery may be hinged to open the resealable delivery channel to receive the spreader and close the resealable delivery channel around the catheter. In some embodiments, the resealable delivery channel may provide a seal around the catheter within the delivery channel. In other embodiments, the resealable delivery channel may close around the catheter without necessarily providing a seal, in which case the lips may close enough to prevent the catheter from buckling and riding out of the delivery channel.

The various embodiments provide improved designs for spreader including shapes for the spreader tip that ease insertion and removal of the spreader through the flexible plastic lips of the resealable delivery channel. For example, the spreader may have flanges or a bulb shaped tip.

In further embodiments, the resealable delivery channel may be shaped to accommodate the spreader or catheter. For example, the flexible plastic lips may be deflected in certain direction. In alternate embodiments, the flexible plastic lips may be adjustable such that a user can move them in various directions.

FIG. 1 illustrates an example catheter 100 that may be used with various embodiments. The catheter 100 may include a handle portion 102, a tube portion 116 and a tip portion 118. The handle portion 102 may be located at a proximal end of the catheter 100 while the distal end of the tube portion 116 may be inserted into the body of a patient.

The handle portion 102 of the catheter 100 may also include an irrigation port 110, which may be used to introduce water or other fluids to irrigate an operating site of the catheter tip, to lubricate the catheter and ease insertion or retraction in the patient, and so on. The handle portion 102 may also include a back port 120 through which one or more wires or cables 112 may leave the handle portion 102. Cables 112 may supply power to the catheter 100 and/or may provide a connection for transmitting (and/or receiving) signals, such as sending (and/or receiving) commands from a remote controller or other control device to the catheter, relaying data from one or more transducers present on the catheter, and so on.

The handle portion 102 may include actuators to control the behavior of the catheter 100. For example, the handle portion 102 shown in FIG. 1 includes a front flange 104a and rear flange 104b that may be squeezed together or pulled apart such that the inner cylinder 108 slides back and forth inside the outer cylinder 106. The sliding motion of the inner cylinder 108 may be transferred along the tube portion 116 to move the tip 118 and/or may actuate one or more mechanisms at the tip 118 of the catheter.

In various embodiments, a variety of different types of catheters may be used with different actuators or functions, such as actuators for deflecting the tip of the catheter to ease navigation inside a patient or for controlling one or more transducers at the tip (e.g., electrical leads, one or more sensor devices, ultrasound devices, etc.).

Figure 2:
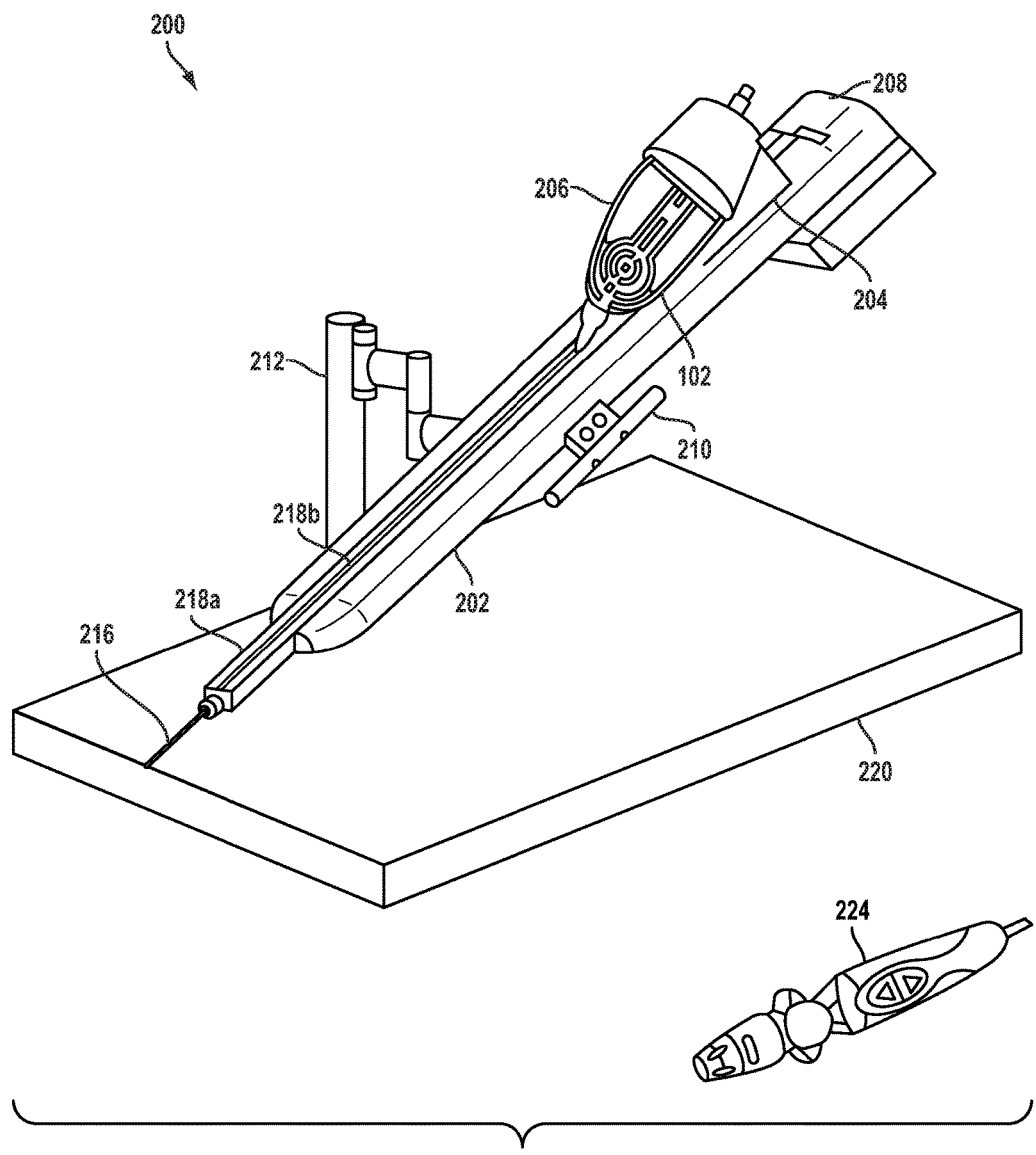
FIG. 2 is an oblique view of a remotely controlled catheter positioning device in suitable for use with the various embodiments.

FIG. 2 illustrates an embodiment catheter positioning device 200 with a remote controller 224. The catheter positioning device 200 may include a sled base 202 coupled with a sled member 204. The sled base 202 may be configured to advance the sled member 204 along the sled base 202 towards the body of the patient or back away from the patient. For example, the sled member may be moved with a motor 208 at one end of the sled base 202. The sled member 204 may move along a rail or other track, such as a worm drive, back and forth along the longitudinal axis of the sled base 202.

The sled base may be mounted with an arm 212 having articulating joints to move the sled base 202 and attached components into various positions, such as over a working surface or an operating table 220. The arm 212 may be extended or rotated to position the sled base 202 relative to a patient on the operating table 220. The sled base 202 may include a handle 210 to move the sled base 202 into position. The sled base may also include a nose cone 216 that may be inserted into a patient. Alternately, the nose cone 216 may connect with an introducer or sheath that may be inserted into the patient. A catheter may be advanced along the sled base 202 and then through the nose cone 216 into the patient.

The sled base 202 may include a sterile barrier in the form of a resealable delivery channel 218a to protect and guide the catheter along the sled base as it is advanced by the sled member 204. For example, the catheter may be inserted into the delivery channel 218a and then the catheter handle 102 may be connected to the sled member 204 (such as by using the modular plate 206 discussed below) such that the catheter is driven forward by translation of the sled member 204 along the resealable delivery channel 218a in the sled base 202 and through the nose cone 216 into the patient.

The resealable delivery channel 218a may be flexible to allow the catheter to be inserted and removed repeatedly. For example, the resealable delivery channel may have a resealing groove 218b with flexible plastic lips running along the top of the delivery channel along the longitudinal axis of the sled base 202. The catheter may be pushed through the resealing groove 218b to position it inside the resealable delivery channel 218a where it may be held in place by the spreader 402 (see FIG. 4). As described in more detail below, the plastic lips may separate to let the catheter pass then come back together to seal behind the catheter. The catheter may be removed by pulling the catheter back through the flexible plastic lips of the resealing groove. In some embodiments the plastic lips may not form a complete seal, but rather may separate and close around the catheter sufficient to prevent buckling of the catheter but without forming a seal.

The sled member 204 may be coupled with a modular plate 206 to which a catheter handle 102 may be attached. Various embodiments may include many alternate modular plates 206 that provide a consistent interface with the sled member 204, while providing different catheter interfaces. Modular plates 206 that may accommodate different catheter types while mating with the sled member 204 may be swapped out so that the catheter positioning system may be used with many different types of catheters. Depending on the kind of catheter that is desired for a procedure, an appropriate catheter-specific modular plate 206 may be selected and attached through the common interface to the sled member 204. The specific type of catheter may be attached to the catheter-specific modular plate 206. The modular plate 206 may also provide catheter-specific actuator interfaces to integrate with any actuators on the catheter handle 102, while providing a common actuator interface for engaging actuator controls of the catheter positioning system, thereby allowing an operator to control the actuators via the remote controller 224.

The sled member 204 may rotate, thereby rotating a catheter connected to the modular plate 206. The sled member 204 may also move linearly along the sled base 202, thereby inserting or extracting a catheter connected to the modular plate. The rotational and translational or linear movement of the sled member 204 may be controlled remotely via the remote controller 224. By controlling translation along the sled base 202, rotation of the sled member 204, and actuation of the catheter's handle via the modular plate 206, an operator may position or use the catheter in any way necessary for a desired operation. Further, an operator may control each of these degrees of freedom (i.e., translation, rotation, and actuation) remotely with the remote controller 224.

Figure 3:
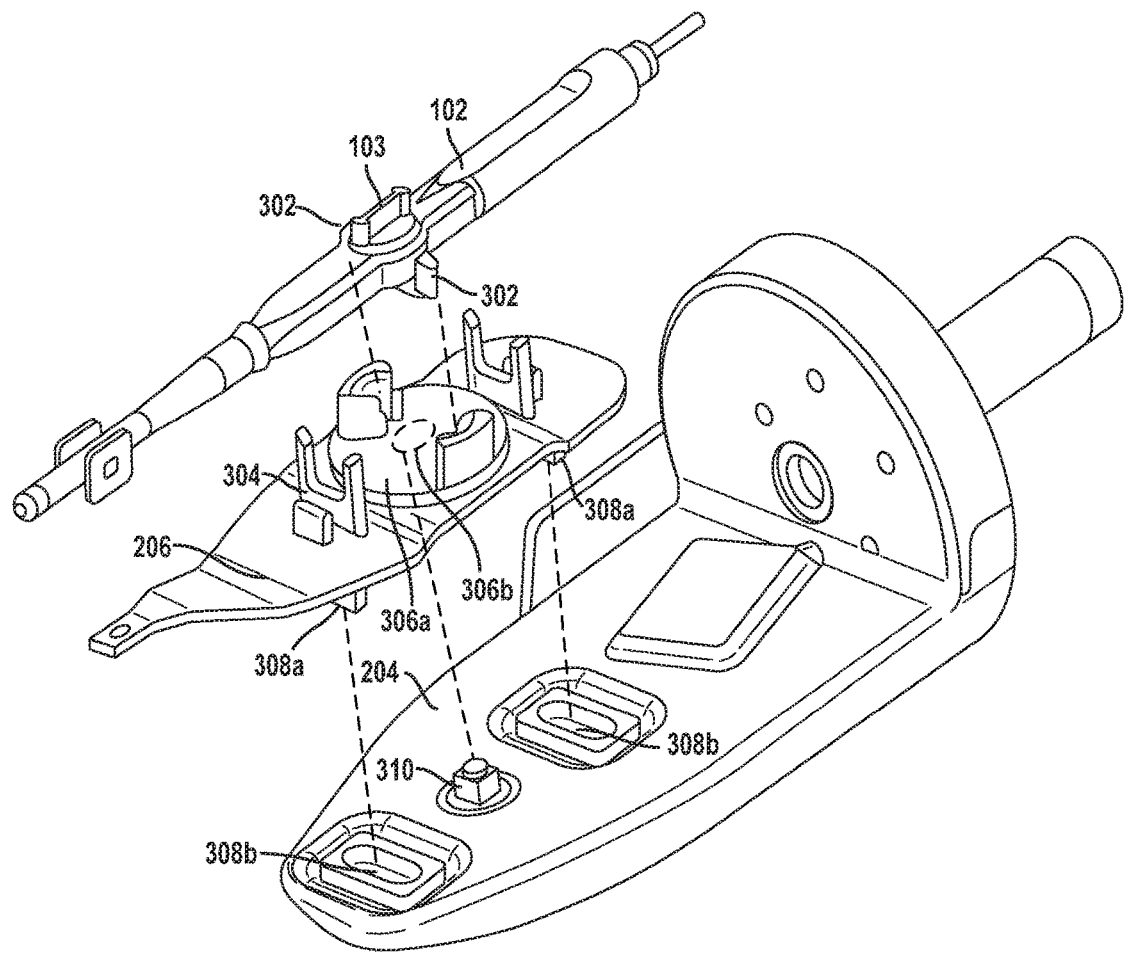
FIG. 3 is an exploded view of a catheter handle portion, a modular plate, and a sled member suitable for use with the various embodiments.

FIG. 3 illustrates an exploded view of a catheter handle 102, modular plate 206, and sled member 204. The catheter handle 102 may include one or more actuators 302 to actuate movement of the catheter, such as extension or retraction of the catheter. In some embodiments, the catheter handle 102 may be provided with a rotatable lever 103 to manually control movement of the catheter. In some embodiments, movement of the rotatable lever 103 may be activated by the actuators 302. In other embodiments, the actuators 302 may control additional or alternative movements of the catheter. As discussed above, the modular plate 206 may be swapped in and out so that various catheters with different actuators may be connected to the catheter positioning device. FIG. 3 illustrates a modular plate 206 that includes clamps 304 to secure the catheter handle 102 as well as a molded nest 306a configured to integrate with the actuator 302 such that the rotatable lever 103 may be controlled by rotating the molded nest 306.

The modular plate 206 may be rigidly, or semi-rigidly connected to the sled member 204 such that translation or rotation of the sled member is transferred through the modular plate 204 to the catheter handle 102 to drive and position the catheter. The sled member 204 and modular plate 206 may be connected by one or more detachable joints, such as a socket 308b that may receive a tab 308a of the modular plate 204. The sled member 204 may also include a control mechanism 310 to integrate with the modular plate 206. The control mechanism 310 may allow the operator to control the catheter's actuators 302. For example, the control mechanism 310 may be a cam or projection that may fit in a corresponding socket 306b of the molded nest 306a. The operator may thereby control the actuators 302, such as by controlling (e.g., rotating) the molded nest 306a through rotation of the control mechanism 310 in the socket 306b. The socket 306b and the control mechanism 310 may be of a common or universal mechanical configuration regardless of the catheter configuration for the modular plate 206. Thus, control mechanism 310 may integrate with any of the various modular plates 206, which may be differently configured to connect with different catheter handles.

Figure 4:
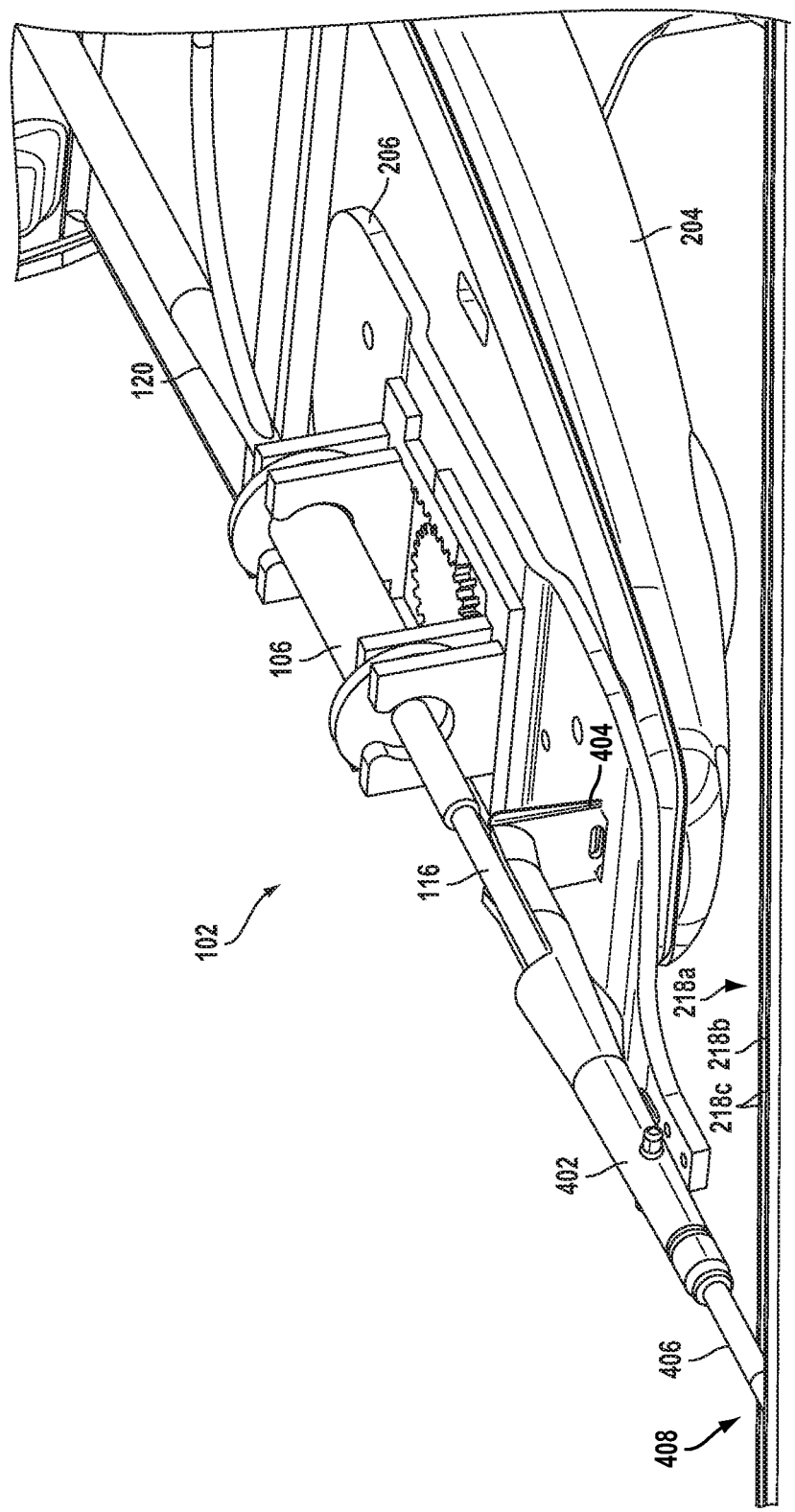
FIG. 4 is an oblique view of a catheter handle portion, a modular plate, and a sled member coupled together suitable for use with the various embodiments.

FIG. 4 illustrates a catheter or catheter-related component, such as the tube portion 116 connected with the modular plate 206 and sled member 204. The spreader 402 may be used to insert the catheter or catheter-related component such as the tube 116 into the resealable delivery channel 218a. As shown in FIG. 4, the spreader 402 may be attached to the modular plate 206 and may be configured to lead the catheter's tube portion 116 into the resealable delivery channel 218a. As the sled member 204 is advanced, the tip 408 of the spreader 402 may remain inside the resealable delivery channel 218. The tip 408 may move the plastic lips 218c of the resealable delivery channel 218a aside so that the catheter tube 116 does not actually come into contact with the plastic lips 218c. Thus, the spreader 402 performs the task of spreading the lips 218c of the resealable delivery channel 218a at the point of the insertion of the catheter 116. As the sled member 204 advances down or retreats up the sled base 202, the spreader 402 and, thus, the point of the insertion of the catheter 116 into the channel, advances or retreats. The plastic lips 218c may be urged or spread open by the spreader 402, such as to accommodate the spreader 402 in the advancing or retreating direction and may close behind the spreader 402 as it moves. Thus, the spreader 402 ensures that forces from plastic lips are not applied to the flexible catheter, ensuring that rotational movement of the catheter is not impeded. In other words, pressure from the plastic lips 218c that may ordinarily pinch against the catheter or tube portion 116 are avoided through the use of the spreader 402.

The spreader 402 may include an attachment portion 404 configured to attach the spreader to the sled member 204 or the modular plate 206. At the other end, the spreader 402 may include a tubular extension or main portion 406 that separates the lips 218c of the resealable delivery channel 218a as the sled member advances and retreats, and a tip portion 408, which is illustrated as hidden within the groove 218b of the resealable delivery channel 218a. The tip portion 408 may remain within the resealable delivery channel 218a. The catheter may emerge from the tip portion 408, such as from inside the groove 218b of the delivery channel 218a.

Figure 5:
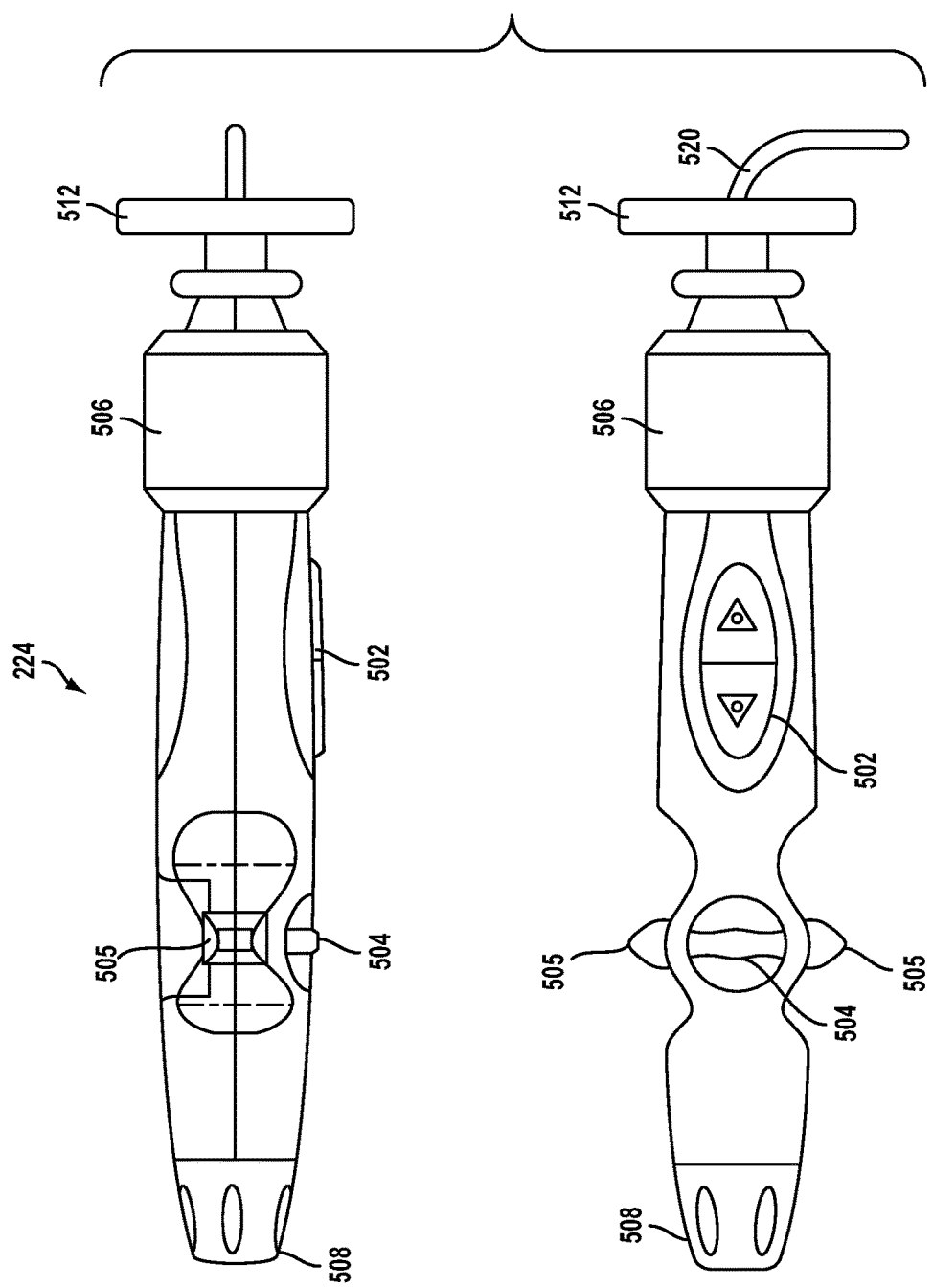
FIG. 5 is a top and side view of a remote controller suitable for use with the various embodiments.

FIG. 5 illustrates an example remote controller 224 from a side and top perspective. The remote controller 224 may include buttons 502 for generating signals for controlling the "in" and "out" (e.g., extension and retraction, forward and backward, etc.) motion of a catheter provided by sliding the sled member 204 up or down the sled base 202. The remote controller 224 may include a dial 508 at one end for controlling rotation of the catheter by generating signals for rotating the sled member 204. The remote controller 224 may also include a rotatable knob 504 and movable knobs 505 that may send control signals to the sled member to control actuation of one or more actuators, such as actuators 302, the rotatable lever 103, and possibly other controls that may be on the catheter handle 102. The remote controller 224 may also include a rotatable sleeve 506 that may be rotated to provide an additional user input, such as a user-designated input, or an input for one or more additional controls that may be available on the catheter. The remote controller may also include a push pull user input device 512 that may similarly be configured to generate signals to control actuation of another catheter element. In embodiments, the control signals generated by operation of the user inputs may be sent from the remote controller 224 to the catheter positioning device via a wire 520 (or wires). Alternatively or additionally, the control signals may be sent wirelessly via a transmitter or transceiver module (not shown).

Figure 6:
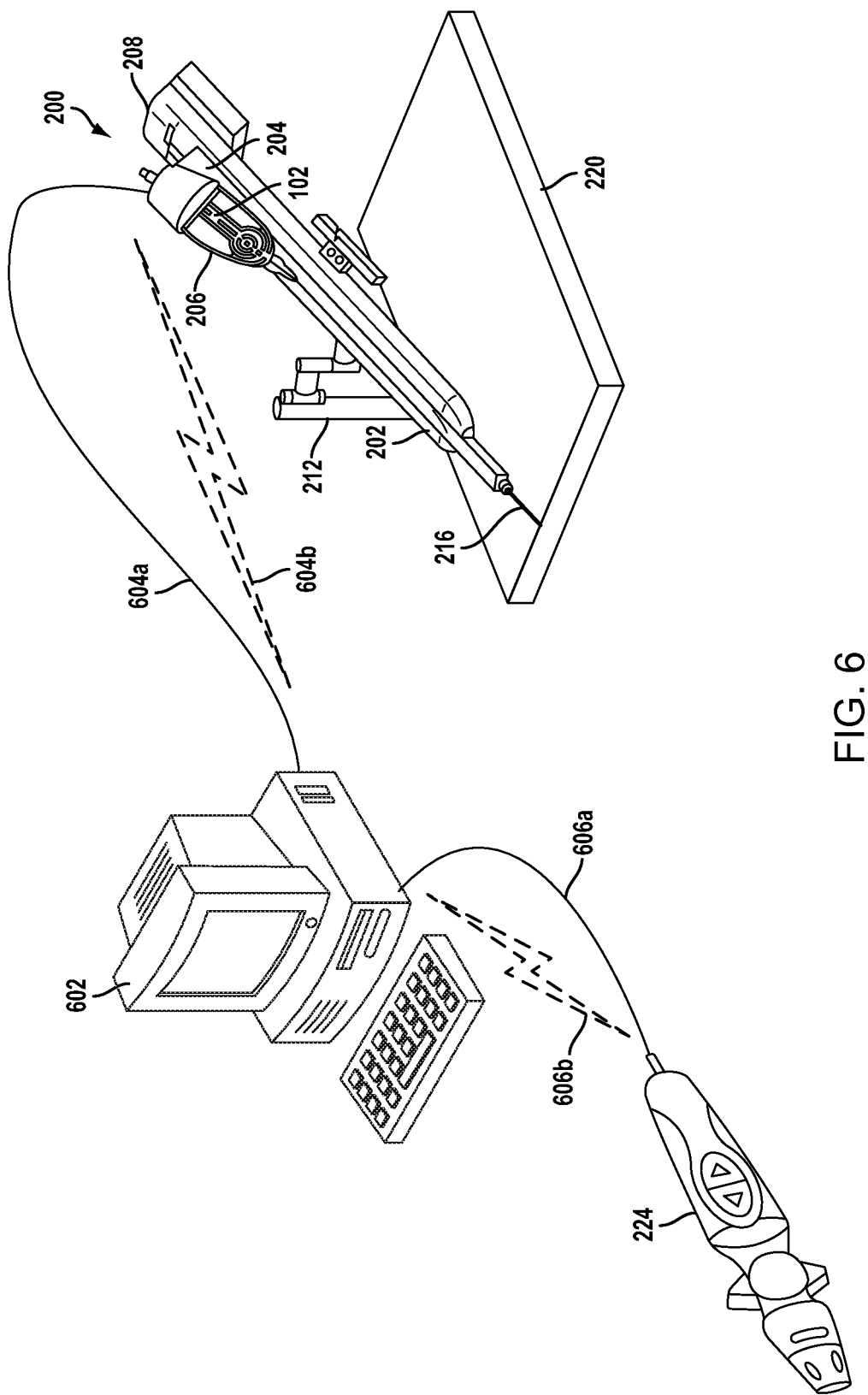
FIG. 6 is a system block diagram illustrating a remote controller, a remotely controlled catheter system, and a programmable control system suitable for use with the various embodiments.

FIG. 6 illustrates a programmable control system 602 as a part of the catheter positioning system. A remote controller 224 may be connected to the programmable control system 602 by a wired connection 606a or a wireless connection 606b such as a wireless data link. The programmable control system 602 may be connected to the catheter positioning device 200 by a wired connection 604a or a wireless connection 604b such as a wireless data link. The connections between the programmable control system 602 and the remote controller 224 and/or the catheter positioning system 200 may be any of a variety of available communication interfaces and/or protocols. Alternatively or additionally, the communications may be at least partially proprietary. In some embodiments, the communications may be secure or at least partially secure to protect patient privacy.

Figure 7A:
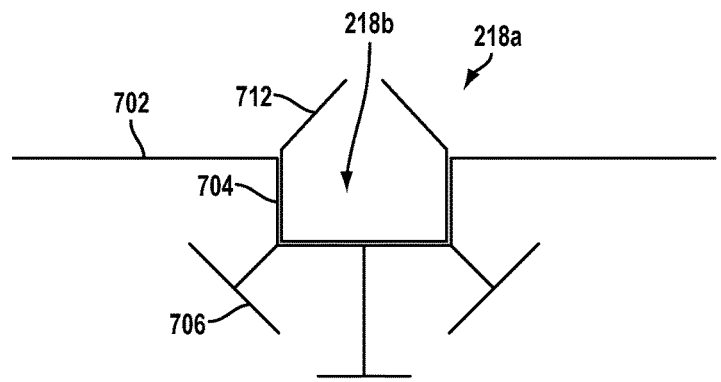
FIG. 7A and FIG. 7B are profile views of an embodiment sterile barrier and resealable delivery channel suitable for use in a catheter positioning system.
Figure 7B:
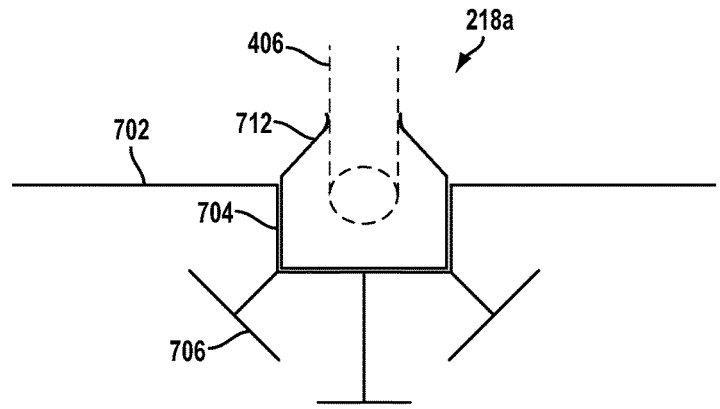

As discussed above, the sled base 202 may be fitted with a sterile barrier including a resealable delivery channel 218 configured to receive and guide the catheter along the sled base as it is advanced by the sled member 204. FIG. 7A and FIG. 7B illustrate a profile of the sterile barrier 702 with the resealable delivery channel 218a. The sterile barrier 702 may have one or more supports 706 to secure into the sled base 202. The resealable delivery channel 218a may include two flexible plastic lips 712 (e.g., 218c) that extend along the length of the resealable delivery channel 218a to form a resealable enclosure around the groove 218b of the resealable delivery channel 218a. As described above, the tube portion 116 of the catheter is guided between the flexible plastic lips 712 by a spreader 402 and into the groove 218b of the resealable delivery channel 218a. The catheter may extend in the groove 218b along the length of the sled base 202 and into a nose cone 216 (as shown in FIG. 2), introducer, sheath or other catheter-holding component and into the patient.

Figure 7C:
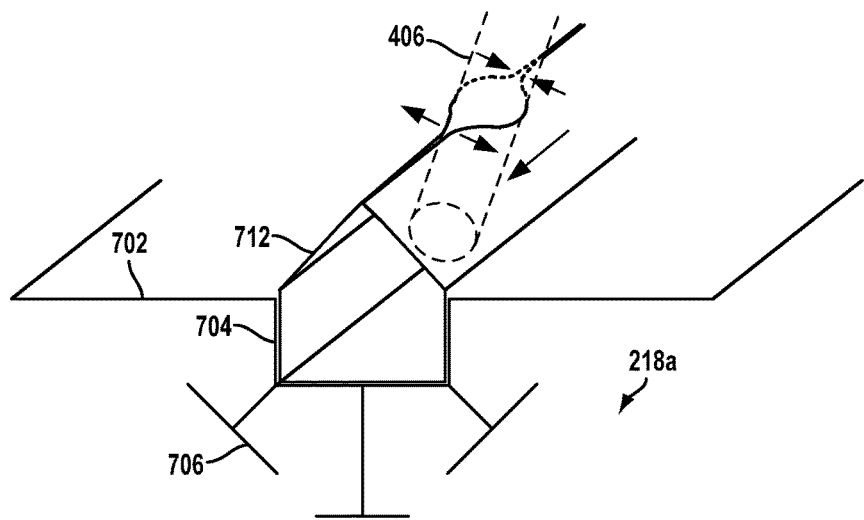
FIG. 7C is a perspective view of an embodiment sterile barrier and resealable delivery channel of FIG. 7A and FIG. 7B suitable for use in a catheter positioning system.

As illustrated in FIG. 7C, the flexible plastic lips 712 may separate to let the main portion 406, and the tip of the spreader 402 pass while holding the body of the main portion 406 within the channel. The lips 712 may come back together to seal or close behind the main portion 406 of the spreader 402 guiding the catheter. In some embodiments, the lips 712 may open in front of and close behind the spreader 402 sufficient to hold the catheter within the channel without forming a seal. As the catheter is positioned, the end of the spreader 402 may stay inside the resealable delivery channel 218a by moving between the flexible lips 712. In other words, the flexible lips 712 may be sealed along the length of the resealable delivery channel 218 except around the spreader 402. The flexible lips 712 may open and close around the spreader 402 as the catheter is advanced and/or retracted.

Figure 8:
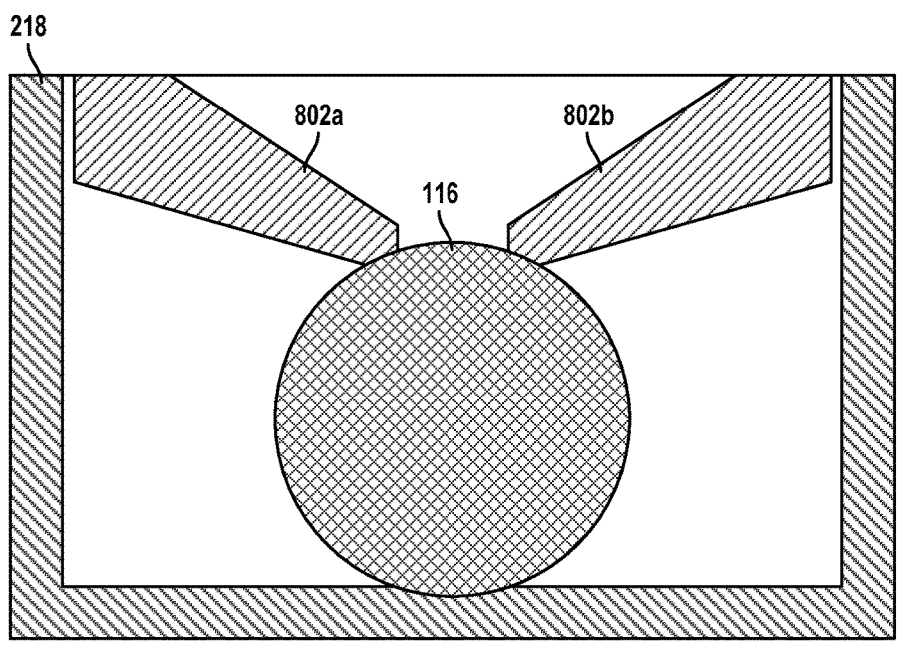
FIG. 8 is a profile view of an embodiment resealable delivery channel with inward slanted flexible lips.

FIG. 8 illustrates a profile of an embodiment resealable delivery channel 218 with a catheter tube portion 116 inside. In an embodiment, the resealable delivery channel 218 may have flexible lips 802a, 802b that slant inward with respect to the resealable delivery channel 218. Flexible lips 802a and 802b having an inward slant may allow catheters or spreaders to more easily be pushed into the resealable delivery channel 218. The shape and configuration of the flexible lips 802a and 802b may also help keep catheters inside the resealable delivery channel as the inwardly-oriented lips 802a, 802b can apply an inward-directed spring force on the catheter 116 to reduce the opportunity for portions of the catheter to pop out of the channel.

Figure 9A:
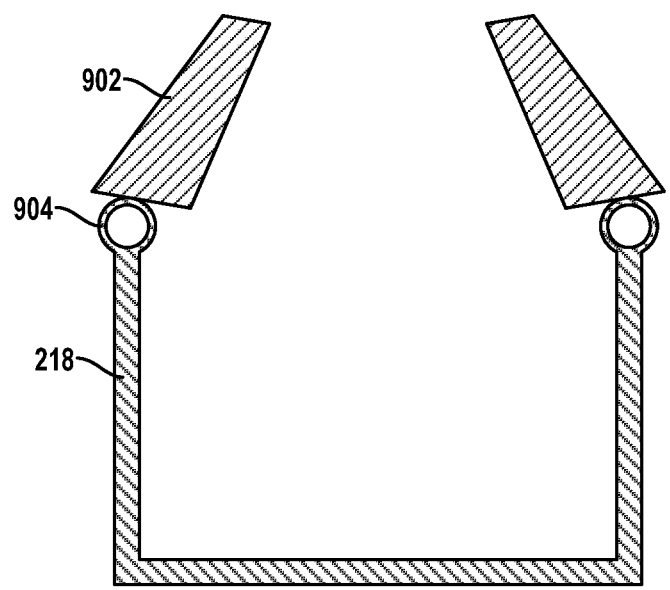
FIG. 9A and FIG. 9B are profile views of an embodiment resealable delivery channel with hinged flexible lips.
Figure 9B:
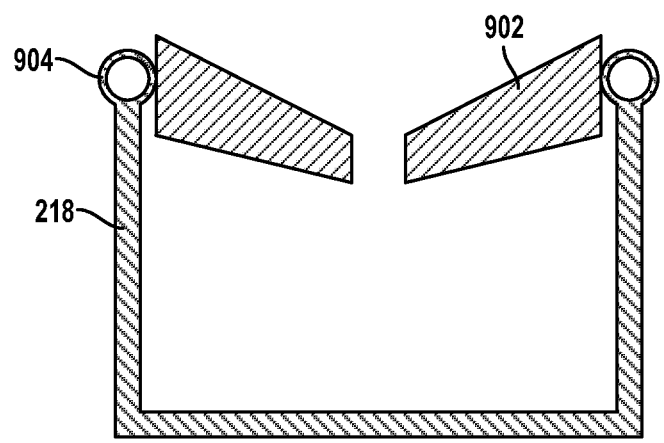

FIG. 9A and FIG. 9B illustrate another embodiment of a resealable delivery channel 218 with flexible lips 902 that may be coupled to the delivery channel 218 by a joint or hinge 904. A lip 902 may be coupled on each side of the channel with a respective joint or hinge 904. In the illustrated embodiment, the full length of the flexible lips 902 may pivot about the joint/hinge 904 to enable easy insertion or removal of the catheter. For example, in the illustrated embodiment, the lips 902 may be moved (i.e., opened and closed) along the entire length, rather than flexing locally, such as where a spreader is inserted. FIG. 9A illustrates the lips 902 in an upward rotated configuration (e.g., in an open configuration). The open configuration of the lips 902 may make it easier to insert a catheter and spreader into the resealable delivery channel 218. FIG. 9B shows the lips 902 in a downward rotated configuration (e.g., in a closed configuration). The closed configuration of the lips 902 may help secure a catheter or spreader inside the resealable delivery channel 218. FIG. 9A and FIG. 9B show lips 902 that are inwardly slanted in a manner similar to the embodiment lips 802a and 802b shown in FIG. 8. In alternate embodiments, lips may be differently shaped and oriented, such as horizontally oriented, or upwardly slanted such as lips as 702 illustrated in FIG. 7, or may be configured according to other orientations, shapes and configurations, while functioning to retain and seal or otherwise contain a catheter, spreader, tube portion, or other catheter-related component.

In alternate embodiments, rather than rotating about a hinge, the flexible lips may move on different types of joints or movement mechanisms. For example, the flexible lips may move up and down or side to side within a mounting mechanism or securing mechanism.

The various embodiments also include improved spreader configurations, including different shaped tips (e.g., a curved tip, flanged tip, bulb tip, etc.) configured to work in conjunction with the resealable delivery channel 218.

Figure 10:
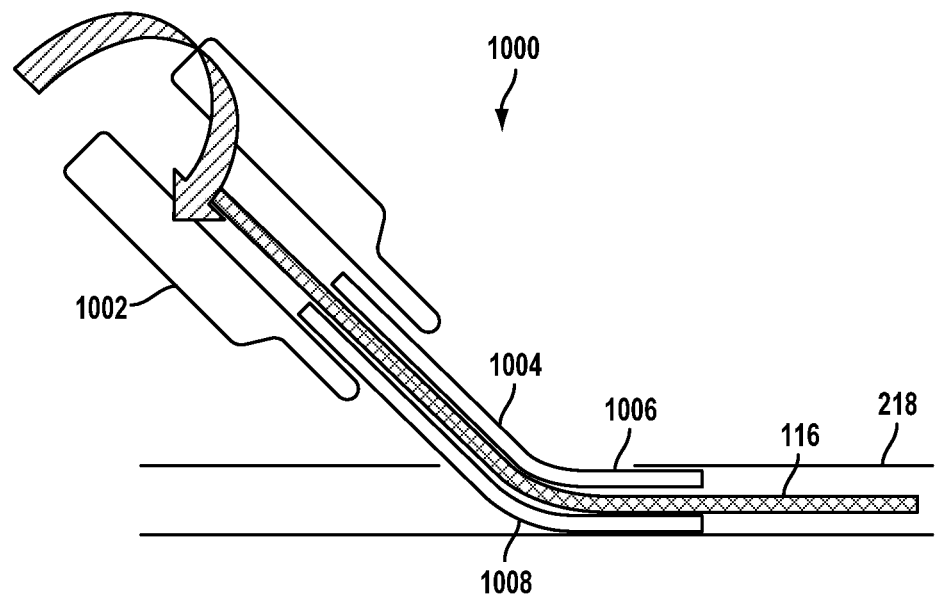
FIG. 10 is a profile view of a spreader with a tip guiding a catheter into a resealable delivery channel according to an embodiment.

FIG. 10 illustrates an embodiment spreader 1000 that includes a main portion 1002, which may be rigid and coupled to a modular plate or sled member, and a tip portion 1004 extending from the main spreader portion 1002. In the illustrated embodiment, the catheter or tube portion 116 may pass through the spreader main portion 1002 and tip portion 1004 and into the resealable delivery channel 218.

The spreader tip portion 1004 may fit into the resealable delivery channel, such as by passing between the flexible lips of the resealable delivery channel 218, as described above. The tip portion 1004 may be curved (as illustrated) or angled to redirect the catheter from the longitudinal axis of the sled member or modular plate to the longitudinal axis of the resealable delivery channel 218.

In an embodiment, the spreader 1000 may have a rotatable tip. For example, the main portion 1004 of the spreader 100, such as the portion that may separate the lips of the resealable delivery channel 218, and the tip portion 1006 from which the catheter or tube portion 116 emerges, may be free to rotate with respect to the spreader attachment portion 1002. In this way, the spreader attachment portion 1002 may rotate with the sled member and/or modular plate as the catheter is rotated into position, while the tip portion 1006 may stay aligned with the resealable delivery channel 218. Allowing the main portion 1004 and the tip portion 1006 to rotate independently, enables the main portion 1004 and the tip portion 1006, which may feature a curve or bend 1008 to be rotated into various positions that may not be otherwise possible. In other words, the main portion 1004 and the tip portion 1006 may be connected by a curved portion 1008 such that a longitudinal axis of the main portion 1004 and the tip portion 1006 may be oriented at an angle to one another. The angled orientation enables the main portion 1004 and the tip portion to be independently rotated, and based on the curved portion 1008, to be presented at a favorable angle for parting the flexible lips of the resealable delivery channel 218 regardless of the positioning of the sled member. For example, when the sled member moves, the main portion 1004 may move slightly while the tip portion 1006 may remain aligned with the delivery channel 218 due to the bend 1008, thereby guiding the catheter or tube portion 116 straight into the channel 218. Any form of rotating joint may be used between the spreader attachment portion 1002 and main portion 1004 and the tip portion 1006, including an overlapping sleeve (as illustrated), a slip joint, and a bearing sleeve that permit rotation about a longitudinal axis of the spreader assembly. While a curved portion 1008 is illustrated, a curved joint may also be used that joins the main portion 1004 and the tip portion 1006 such that the main portion may move while the curved joint allows the tip portion 1006 to maintain an alignment along the longitudinal axis of the delivery channel 218, such as to provide a straight path for the catheter 116.

In an embodiment, the spreader main portion 1004 may be flexible, such as more or less flexible than the flexible lips. However, in order to prevent the lips from pinching through the spreader main portion 1004 or the tip portion 1006 and restricting the movement of a catheter or the tube portion 116, the flexibility of the spreader main portion 1004 and/or the tip portion 1006 may be less than the lips. In some embodiments, the spreader may be stiffer than the catheter. Alternately, the spreader main portion 1004 and/or the tip portion 1006 may be rigid with minimal flexibility.

In further embodiments, the spreader main portion 1004 and/or the tip portion 1006 may be fashioned with various shapes configured to help the spreader and catheter to enter the resealable delivery channel 118 and/or remain in the channel during operation while enabling the spreader to spread the flexible lips of the delivery channel as the catheter is advanced or retracted along the sled base. One problem addressed by the above described embodiments is that a spreader may require a diameter that is small enough at the point where the spreader engages the flexible lips of the delivery channel to avoid excessive bending the lips as the spreader is advanced along the sled base. Excessive pressure on the spreader may lead to pinching of a catheter, catheter sheath, tube portion or other catheter related component. However, a small diameter at the tip reduces a force of the lips against the spreader thus reduces the forces keeping the spreader within the delivery channel. Conventional spreaders with a consistent diameter along their length, including portions that project into the delivery channel, may be prone to disadvantages in that such spreaders may inadvertently "pop out" of the delivery channel during operation. Thus, further embodiments may include shapes that reduce the potential for the tip of the spreader to pop out of the delivery channel while presenting an acceptable diameter along the length to avoid over stressing the flexible lips.

Figure 11:
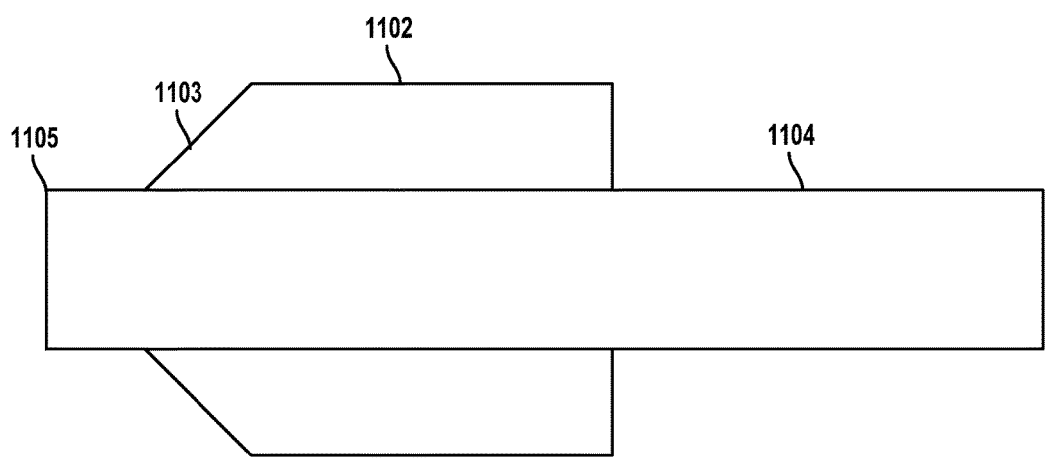
FIG. 11 is a top view of an embodiment spreader with a flanged tip.

FIG. 11 illustrates an embodiment in which the end of a spreader tip portion 1104 may include flanges 1102, such as on opposite sides of the tip portion 1104 that may come into contact with the delivery channel 218. The flanges 1102 may be configured to hold the spreader within the delivery channel 218. The flanges 1102 may be configured with portions 1103 that are tapered towards the distal end 1105 of the tip portion 1104. The tapered portions 1103 may ease insertion of the tip portion 1104 into the resealable delivery channel. Tapered flanges 1102 may help separate the flexible lips as the spreader is inserted.

Figure 12A:
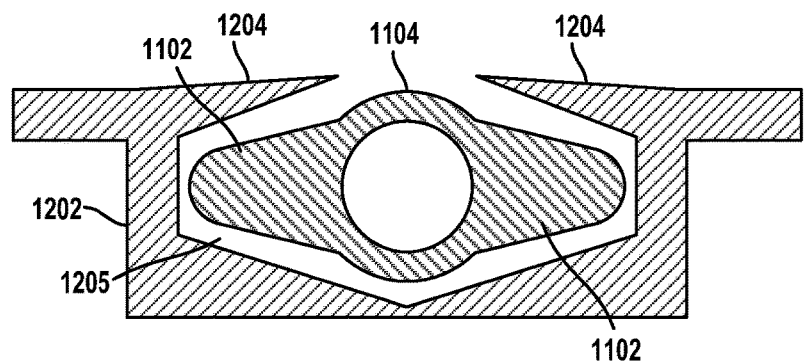
FIG. 12A is a profile view of an embodiment resealable delivery channel shaped to fit a spreader with a flanged tip.

In further embodiments, the resealable delivery channel 218 may be configured with an internal shape 1203 that is shaped to guide the spreader tip portion 1104, such as when the spreader tip portion 1104 is configured with flanges 1102. For example, FIG. 12A illustrates an embodiment in which the end of a spreader tip portion 1104 may be configured with a profile that is compatible with that of the internal shape 1203 of the resealable delivery channel 1202. In other words, the spreader tip portion 1104 configured with flanges 1102 may be configured with a profile that fits into the internal opening or internal shape 1203 of the delivery channel 1202. The shaped resealable delivery channel 1202 may include flexible lips 1204. At least an inner portion of the lips 1204 may have a shape that conforms with or is compatible with the shape of the spreader tip portion 1104. The shaped resealable delivery channel 1202 may constrain the movement of the spreader tip 1104 and the flanges 1102 to a substantially straight path along the delivery channel 1202 as the catheter is advanced, retracted, and/or rotated.

Figure 12B:
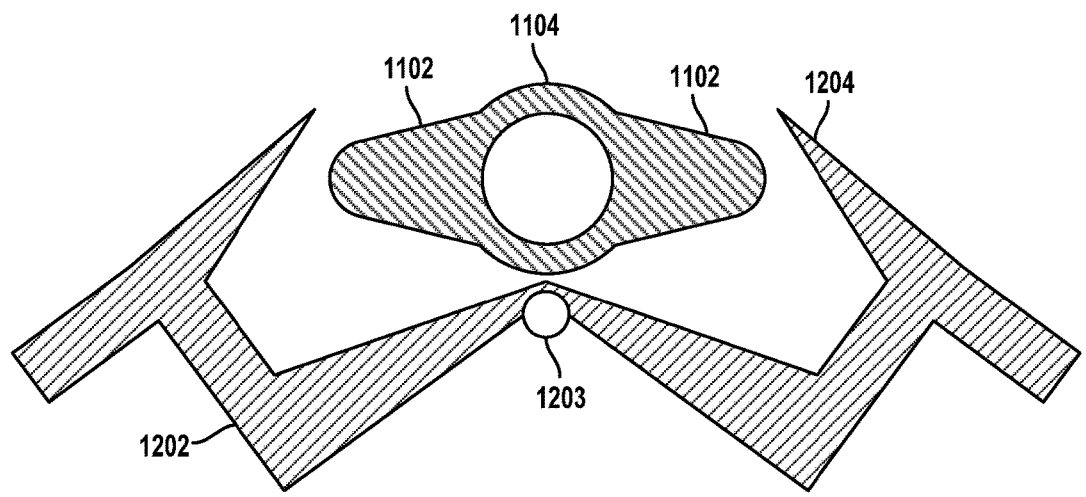
FIG. 12B is a profile view of another embodiment resealable delivery channel shaped to fit a spreader with a flanged tip.

FIG. 12B illustrates an embodiment in which the resealable delivery channel 1202 may include a hinge 1203 enabling the resealable delivery channel 1202 to open. The hinge 1203 may run the entire length of the channel portion of the resealable delivery channel 1202 dividing the resealable delivery channel 1202 into two portions each including its own flexible lip 1204 and rotationally coupled together by the hinge 1203. The resealable delivery channel 1202 may be opened by rotating the two portions away from each other around the hinge 1203. When in an open position, the flexible lips 1204 may be farther apart from each other than when positioned in a closed position. The space between the flexible lips 1204 may more easily accommodate the spreader tip portion 1104 with the flanges 1102. The spreader tip portion 1104 with the flanges 1102 may be placed in the resealable delivery channel 1202, and the two portions of the resealable delivery channel 1202 may be rotated toward each other around the hinge 1203 to contain the spreader tip portion 1104 and the flanges 1102. The closed delivery channel 1202 may constrain the movement of the spreader tip 1104 and the flanges 1102 to a straight path along the delivery channel 1202 as the catheter is advanced, retracted, and/or rotated. In embodiments, the hinge 1203 may be any form of hinge, including a thinned section that is flexible due to its reduced thickness, a flexible material joining the two portions of the delivery channel 1202 that enables bending, and a mechanical hinge that may be any type of known hinge, including a barrel hinge, pivot hinge, butt & mortise hinge, a case hinge, a piano hinge, a flat hinge, an H hinge and an HL hinge.

Figure 13:
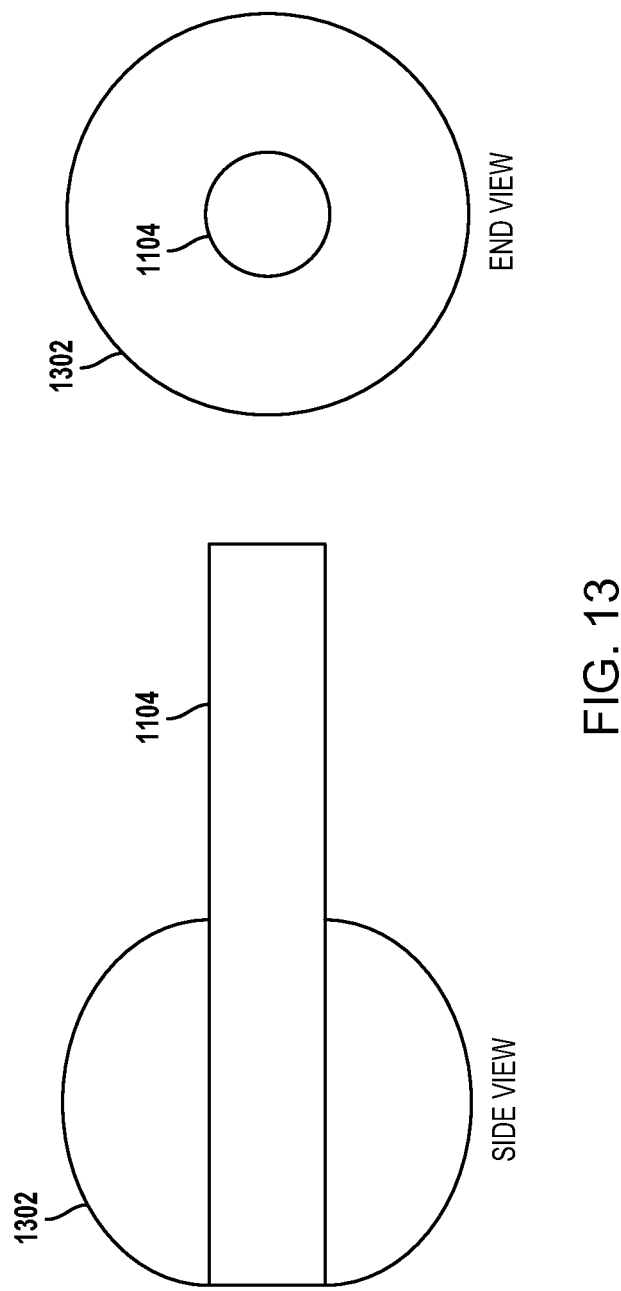
FIG. 13 is a side view of an embodiment spreader with a bulb tip.

FIG. 13 illustrates another embodiment spreader tip portion 1104 including a spherical or bulb-shaped tip 1302. In the illustrated embodiment, the spreader tip portion 1104 with the bulb tip 1302 may be easier to push in or pull out through the flexible lips of the resealable delivery channel. The bulb shaped bulb tip 1302 provides a larger radius than the spreader tip portion 1104. When inside the delivery channel, the bulb tip 1302 may interact with the flexible lips to prevent the spreader 1104 from inadvertently popping out of the resealable delivery channel.

Figure 14:
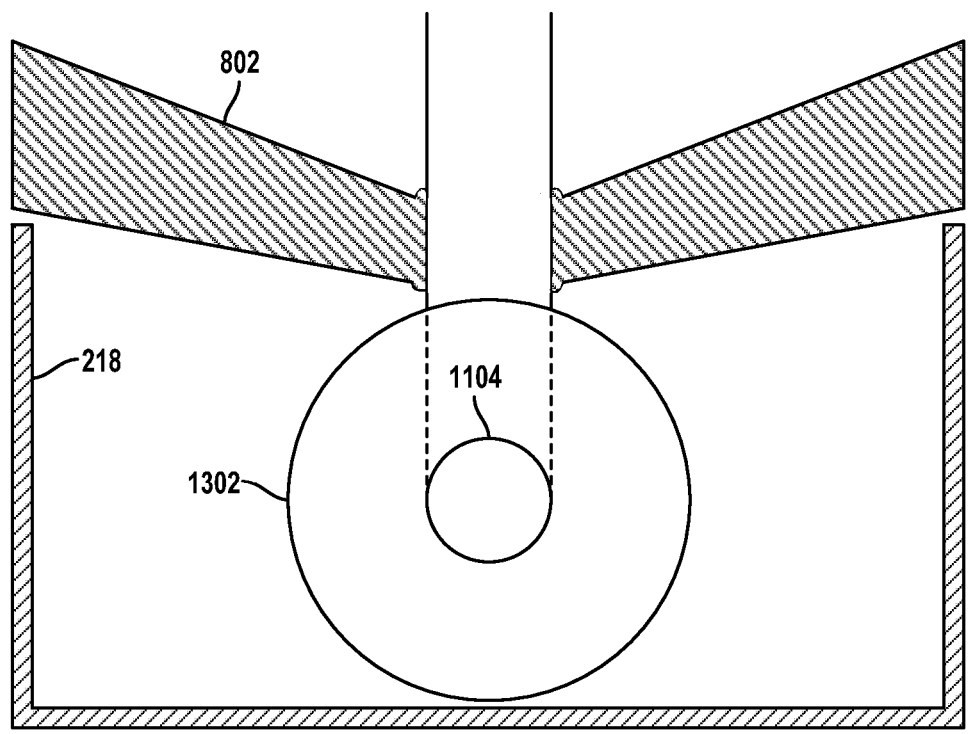
FIG. 14 is a profile view of an embodiment resealable delivery channel with a spreader with a bulb tip.

FIG. 14 illustrates a profile of a resealable delivery channel 218 with a bulb tip spreader 1302 positioned beneath the flexible lips 802. As illustrated, the flexible lips 802 will present greater resistance to withdrawal of the bulb tip 1302 of the tip than the thinner diameter of the spreader tip 1104. Further, when the lips 802 are configured in a downward facing orientation, a natural resistance to upward movement of the bulb tip 1302 will be presented. In other words, as an upward force is exerted on the bulb tip 1302, and correspondingly on the inner surfaces of the lips 802, the lips 802 will press more forcefully on the sides of the spreader tip 1104. A progressively increasing upward force on the bulb tip 1302 may provide progressively increasing resistance to removal of the bulb tip 1302 from the delivery channel 218. In this manner, when the portion of the spreader 1104 that passes through the flexible lips 802 of the delivery channel 218, such as the bulb tip 1302, has a diameter just a little larger than a gap between the flexible lips, the bulb tip 1302 may be held in place within the channel 218 by the flexible lips 802.

Figure 15:
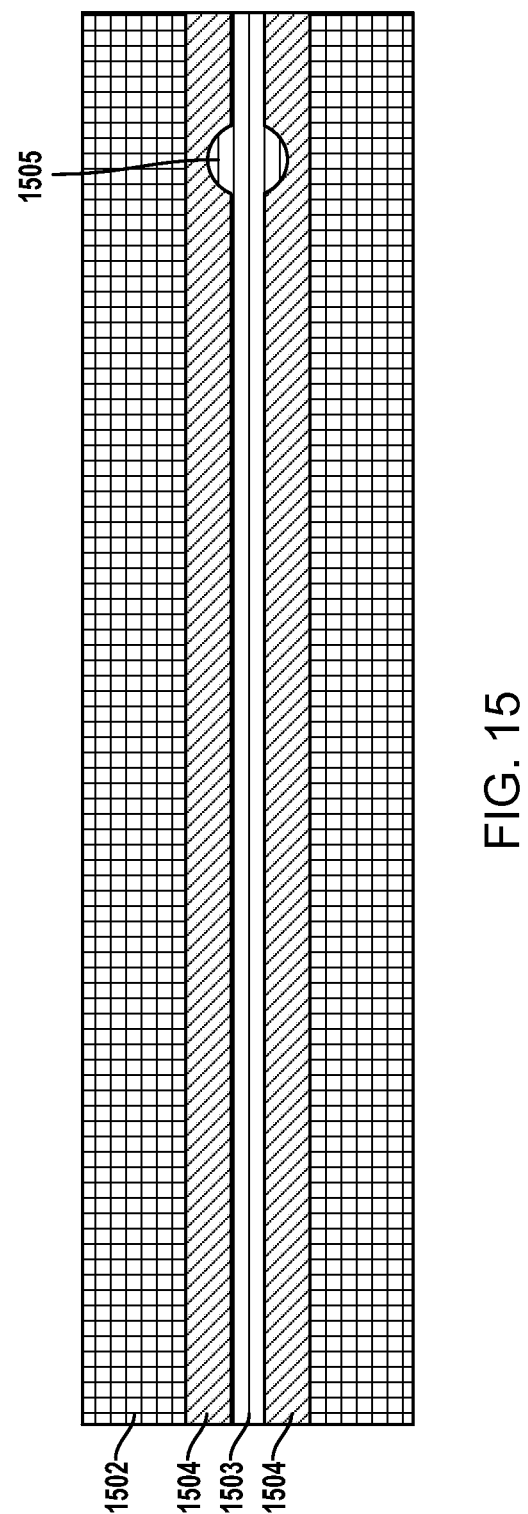
FIG. 15 is a top view of an embodiment resealable delivery channel in a sled base.

FIG. 15 illustrates a top view of an embodiment resealable delivery channel 1503 inserted in a sled base 1502. In an embodiment, the flexible lips 1504 of the resealable delivery channel 1503 may be configured to include cutouts or other modifications formed in the flexible lips 1504 that result in one or more entry holes 1505 to enable tip of the spreader to easily slide into the track of the resealable delivery channel 1503, such as in the area of the entry hole 1505. The tip of the spreader, such as the bulb tip 1302, may be easily inserted into the entry hole 1505 while being constrained by the lips 1504 within the other portions of the delivery channel 1503. The one or more entry holes 1505 may be located in a portion of the resealable delivery channel 1503 that the spreader may not cross during normal operation, such as at a proximal end of the sled base 1502 located away from a patient.

As discussed, the flexible plastic lips 1504 may include features, such as semi-circular cutouts, that form the one or more entry holes 1505 to enable the spreader to easily slide into the resealable delivery channel in the area of the entry holes 1505. Once inserted, part or all of the spreader may move with the catheter during positioning, such as rotating with the catheter. The resealable delivery channel 1503 may additionally be hinged to open the resealable delivery channel to receive the spreader and to close the resealable delivery channel around the catheter as described herein above.

Those skilled in the art will recognize that the methods and systems of the present invention have many applications, may be implemented in many manners and, as such, is not to be limited by the preceding exemplary embodiments and examples. Additionally, the functionality of the components of the preceding embodiments may be implemented in different manners. Further, it is to be understood that the steps in the embodiments may be performed in any suitable order, combined into fewer steps or divided into more steps. Thus, the scope of the present invention covers conventionally known and future developed variations and modifications to the system components described herein, as would be understood by those skilled in the art.

What is claimed is:

1. A catheter positioning system, comprising:
   a modular plate configured to receive a proximal portion of a catheter;
   a sled member coupled to the modular plate;
   a sled base configured to advance the sled member towards a patient;
   a resealable delivery channel coupled to the sled base and configured to receive and guide the catheter along a length of the sled base, the resealable delivery channel comprising a channel portion having a slotted opening on top along the length of the channel portion and flexible lips extending toward one another and parallel to the channel portion along opposed sides of the channel portion; and
   a spreader comprising a shaped tip configured to guide the catheter between the flexible lips and into the channel portion, wherein the flexible lips are configured to enable the shaped tip to be inserted into the channel portion by pressing the shaped tip between the flexible lips from above, through the slotted opening on top, and into the channel portion, wherein the shaped tip is wider than a more proximal portion of the spreader such that, while the flexible lips engage opposed sides of the more proximal portion of the spreader, engagement of an underside of the flexible lips with a proximal portion of the shaped tip resists an inadvertent removal of the shaped tip from the channel portion.

2. The catheter positioning system of claim 1, wherein the spreader comprises a rotatable tip portion distal to an attachment portion, wherein the rotatable tip portion freely rotates relative to the attachment portion.

3. The catheter positioning system of claim 1, wherein the shaped tip comprises a bulb-shaped tip portion.

4. The catheter positioning system of claim 1, wherein the shaped tip comprises a flanged tip portion.

5. The catheter positioning system of claim 1, wherein the resealable delivery channel has a cross-sectional shape that conforms to a shape of the shaped tip of the spreader so as to guide the shaped tip within the channel portion.

6. The catheter positioning system of claim 1, wherein an outer side of the flexible lips are configured to slant toward a bottom of the channel portion.

7. The catheter positioning system of claim 1, wherein the flexible lips are attached to the resealable delivery channel by a rotatable joint.

8. The catheter positioning system of claim 7, wherein the rotatable joint comprises a hinge.

9. The catheter positioning system of claim 1, wherein the channel portion includes a hinge enabling the resealable delivery channel to be opened to receive the spreader.

10. The catheter positioning system of claim 1, wherein the flexible lips are configured to include an entry hole with a wider opening than the slotted opening for insertion of the shaped tip into the channel portion.

11. The catheter positioning system of claim 1, wherein the flexible lips are configured to form at least a partial seal around the spreader, wherein the at least the partial seal is movable with the spreader along the length of the sled base.

12. The catheter positioning system of claim 1, wherein the flexible lips are configured to form a full seal around the spreader, wherein the full seal is movable with the spreader along the length of the sled base.

* * * * *